United States Patent [19]

Knoche et al.

[11] 4,127,330
[45] * Nov. 28, 1978

[54] OPTICAL PRESSURE JUMP RELAXATION DETECTOR

[75] Inventors: Wilhelm Knoche, Göttingen; Gottfried Wiese, Sieboldshausen, both of Germany

[73] Assignee: Max-Planck-Gesellschaft zur Förderung der Wissenschaften e.V., Göttingen, Germany

[*] Notice: The portion of the term of this patent subsequent to Feb. 3, 1993, has been disclaimed.

[21] Appl. No.: 788,258

[22] Filed: Apr. 18, 1977

Related U.S. Application Data

[63] Continuation-in-part of Ser. No. 498,816, Aug. 19, 1974.

[30] Foreign Application Priority Data

Feb. 22, 1974 [DE] Fed. Rep. of Germany ....... 2408646

[51] Int. Cl.² ............................................. G01N 1/10
[52] U.S. Cl. ................................................. 356/246
[58] Field of Search .......................... 356/246; 250/576

[56] References Cited

U.S. PATENT DOCUMENTS 3,935,728  2/1976  Knoche et al. ........................... 73/53

Primary Examiner—Vincent P. McGraw
Attorney, Agent, or Firm—Flynn & Frishauf

[57] ABSTRACT

To investigate fast chemical reactions and to obtain an optical output signal, a measuring cell holding a liquid sample is formed with at least two optical windows sealed to a sample chamber to permit placing the sample chamber in the path of an optical detection beam. A pressure generator, for example a liquid being applied against the sample with the interposition of a separating membrane applies pressure on the sample, the pressure then being suddenly released and chemical reactions upon change in pressure optically evaluated by detection of changes in the optical beam.

16 Claims, 5 Drawing Figures

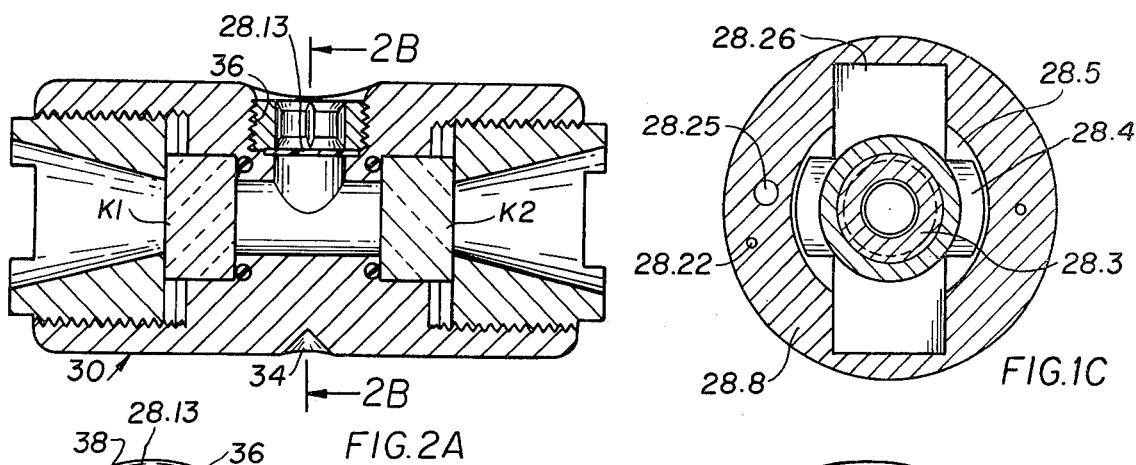
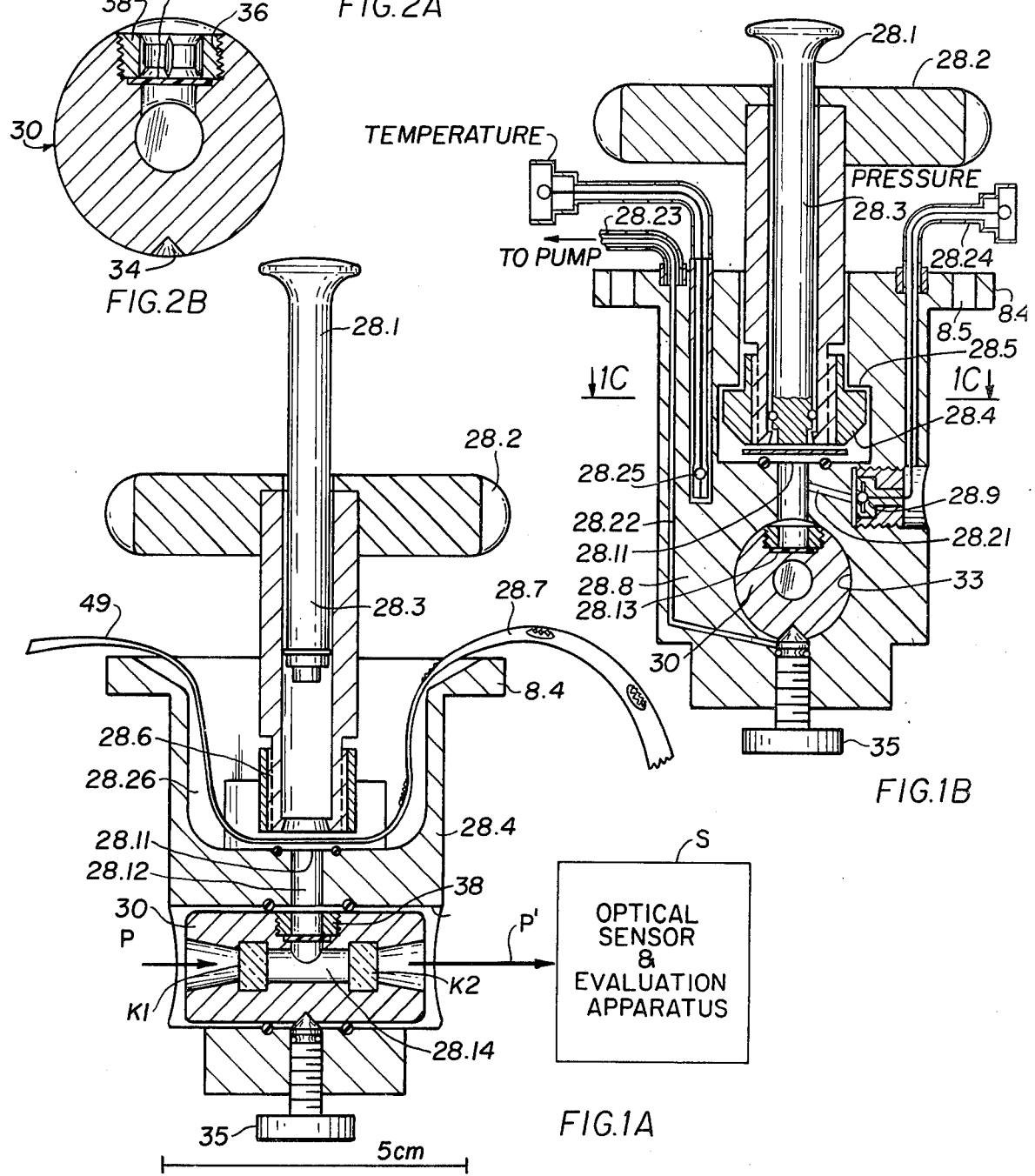

OPTICAL PRESSURE JUMP RELAXATION DETECTOR

The present application is a Continuation-in-Part of U.S. Ser. No. 498,816, filed Aug. 19, 1974 De Maeyer et al, and in which the inventorship was changed by amendment under 35 U.S.C. 116.

Cross reference to related patents and applications

U.S. Ser. No. 498,816, De Maeyer et al., now U.S. Pat. No. 4,076,420, U.S. Pat. No. 3,720,094, KNOCHE; U.S. Pat. No. 3,935,727 KNOCHE and WIESE; all assigned to the assignee of the present application.

The present invention relates to a pressure jump cell which may be used in apparatus disclosed in the parent application Ser. No. 498,816, filed Aug. 19, 1974, now U.S. Pat. No. 4,076,420, Feb. 28, 1978, De Maeyer et al., and more specifically to apparatus which permits optical evaluation of chemical reactions which occur upon disturbance of a chemical equilibrium when pressure applied to a chemical substance is changed.

Many chemical relaxation techniques have been developed which differ in the way they disturb a chemical equilibrium, as well as in the method of observing concentration changes. Reference is made to "Pressure Jump Relaxation Technique with Optical Detection", published in "Review of Scientific instruments," Vol. 47, No. 2, Feb. 1976, pages 220, 221, describing pressure jump relaxation techniques with optical detection, and to which the present invention relates. The references cited in the aforementioned publication are of interest regarding investigation of pressure jump relaxation observation in general. U.S. Pat. No. 3,935,727, by the inventors hereof, describes a pressure jump relaxation measurement apparatus in which electrical outputs are obtained measuring transient electrical variations upon change in pressure applied to a sample medium. The present invention is specifically directed to an apparatus in which optical output signals can be obtained representative of transient phenomena upon changes in pressure applied to a sample medium.

Subject matter of the present invention. Briefly, a body forming an autoclave sample chamber and an auxiliary pressure chamber is provided, the body preferably being of brass. The sample chamber holds a liquid sample, the relaxation pressure characteristics of which are to be investigated. Two optical windows are sealed to the sample chamber to permit placing the chamber in an optical detection beam path. An elastic membrane sealingly separates the chambers, so that the liquid sample can be introduced into the sample chamber and the pressure chamber filled with a pressure fluid, for example water which is pressurized from an outside source. A pressure head is applied to the chamber of the pressure generating means which includes a rupturable membrane so that, when the pressure rises to the breaking point of the rupturable membrane, it is suddenly and explosively released. The explosive release of pressure on the sample causes phenomena to occur in the samples which can be optically investigated by electrically transducing changes in the optical detection path, for example by sensing the output from a photoelectric detector which is in optical relationship to the detection beam path.

Drawings, illustrating an example:

FIG. 1A is a longitudinal schematic sectional view through the apparatus;

FIG. 1B is a longitudinal cross-sectional view taken 90° offset with respect to the view of FIG. 1A, and illustrating the pressure head in closed position;

FIG. 1C is a cross-sectional view taken along line D—D of FIG. 1B,

FIG. 2A is a greatly enlarged detail view of the sample cell used in the embodiment of FIGS. 1A and 1B, and FIG. 2B is a cross-sectional view of the sample cell of FIG. 2A taken along line VI—VI of FIG. 2A.

The pressure jump cell which may be used with the apparatus of application Ser. No. 498,816, filed Aug. 19, 1974, De Maeyer et al., now U.S. Pat. No. 4,076,420, is shown in FIG. 1A using the bursting membrane principle. This cell comprises also an autoclave sample cell 30, an auxiliary pressure chamber 28.12, and an elastic sealing membrane 28.13 between these two chambers. The version shown has been designed for measurements of absorption. FIGS. 1A and 1B give vertical and transverse cross sections through the light path. FIG. 1C is a similar cross section wherein the apparatus is rotated by 90° and more details are given with respect to the auxiliary pressure chamber, and the bursting, or rupturable, membrane 28.7, and the corresponding fixation means. FIG. 1C shows a bayonet head and socket shown from below. A pressure jump apparatus of similar design, using electrical conductivity instead of optical detection method, is described in our U.S. Pat. No. 3,935,727, assigned to the assignee of the present application.

The cell body is preferably of brass or bronze, and screwed onto a cell holder (not shown) by a flange 8.4 and secured by bolts passing through holes 8.5 (FIG. 1B).

The upper opening 28.11 of the pressure chamber 28.12 can be closed off by a bursting, or rupturable, membrane 28.7 (FIG. 1A) in strip form. The advantage of the bursting membrane principle, especially when used in optical systems, are the short pressure release time and the very low inertial forces which practically do not cause any mechanical vibrations of the optical set-up which could affect the stability of the lightsource. The disadvantage of this method was the troublesome time-consuming interchange of membranes after each measurement. This disadvantage, however, has been overcome completely by combining a quick-release pressure head 28.3 with a stripshaped membrane 28.7 — similar to the device already described in the aforementioned U.S. Pat. No. 3,935,727. This permits fast sequencing of measurements and application of averaging techniques which, if performed by digital data storage and computing devices, give kinetic data with a much higher degree of accuracy than before.

Operation: The pressure head 28.3 has a bayonet head 28.4 fitting a bayonet socket 28.5 (FIG. 1C) in the cell body 28.8. The bayonet head has a clamping thread, either at its circumference matching a female thread in the bayonet socket, or between the bayonet head and the pressure heat itself shown as thread 28.6 (FIG. 1A). The bayonet socket has a stop. Thus, when rotating the hand wheel 28.2, the pressure head is lowered — with respect to FIG. 1A — and pressed against the membrane 28.7 which closes tightly against the opening 28.11; a sealing O-ring is also provided (FIG. 1A). After rupturing of a membrane in the strip, the pressure head is released by rotating hand wheel 28.2 in the opposite direction, thus releasing the membrane. A short section of the membrane strip then is pulled through in order to place a fresh zone of membrane material above the chamber opening. The hand wheel 28.2 is tightened again, closing off the pressure chamber anew. Thus, at least 20 pressure jumps may be performed on a single sheet of membrane foil of half a meter length, each part of which is correctly located between the pressure head and the chamber opening, and giving highly reproducible results.

After the cell 28.12 is filled and put into the optical apparatus, a pressure liquid pump is connected via a flexible pressure hose and an easily removable pressure hose connection 28.23 (FIG. 1B) to a pressure supply system. Duct 28.22, terminates beneath the pressure chamber in the region of set screw 35, to propagate through a ring groove formed at the circumference of the cell 30 to the pressure chamber 28.12. The duct 28.22 may have a ball valve (not shown) therein. A pressure gauge should be provided on the pump or with the cell. The pressure is smoothly increased until the membrane bursts. With a brass membrane of 0.1 mm thickness, the bursting pressure is up to 150 atm. Upon pressure release a trigger signal is obtained from a piezoelectric pressure transducer 28.9 (FIG. 1C) which is embedded in epoxy on its outer side and sealed with silicone rubber and is connected with the pressure chamber via the duct 28.21. A pressure measuring signal is available at terminal 28.24 and can be used to trigger measuring and recording instruments. Optical signals derived from the optical path through the windows K1, K2 (FIG. 1A) of the sample cell 30 can be transduced by a photodetector to be then recorded by an oscilloscope or a digital storage device.

In order to obtain a short pressure release time of, say, 50 $\mu s$, the length of the pressure chamber 28.12 (FIG. 1A) is made as short as possible, whereas the distance between the cell chamber windows K1 and K2 may be up to 20 mm in order to obtain a reasonable amplitude with weakly absorbing samples. Larger distances may be used if a longer pressure release time is satisfactory. Briefly, a short distance between the opening 28.11 and the optical axis is needed. With the present construction (where the drawing gives an enlarged length of the auxiliary pressure chamber), this has been achieved by a tube-like gap 28.26 (FIG. 1A) gently guiding the membrane foil which dips deeply into the cell body. Thus, the external dimensions of other cells can be easily matched. A small suction pump (not shown) can be connected to the gap 28.26 to remove leakage pressure fluid.

For pressure fluid, water has been found to be more appropriate than organic liquids such as oils, for two reasons: First, vapors of many organic substances form deposits on ultraviolet (UV)-transmitting and -reflecting optics, especially at high UV-intensities which are preferably used with the apparatus; and, secondly, adiabatic heating due to the applied pressure is approximately ten times less than with many other liquids. Thus, thermal stability is increased. The pressure head 28.3 has been made hollow with a movable piston 28.1 which forms a vacuum pump. O-rings are used for sealing. Before tightening the hand wheel 28.2, the piston is pressed down facing the membrane with a very small gap as shown in FIG. 1C. After the pressure head is closed the piston is drawn back and clamped in its upper position as shown in FIG. 1A. The pressure above the membrane as thus reduced is of the order of 5 mbars. This effectively reduces acoustic noise and pressure wave interferences in the cell chamber 28.14 when the membrane is ruptured.

Precision measurements yielding information on amplitudes and time constants of the studied chemical reactions can be improved by using a calibrated pressure transducer 28.9 and recording both the photodetector and the pressure transducer signals digitally, further feeding them to a digital computer. The contribution of the applied pressure pulse function to the measured data can then be eliminated by the inverse convolution technique.

A temperature sensing probe 28.25 is provided for convenience which measure the stationary temperature in the cell body. As an illustrative size, a dimension mark is given in FIG. 4. The width of the autoclave body, as shown, is approximately 5 cm.

The sample cell 30 is shown in detail in FIGS. 2A and 2B, and permits easy exchanging and filling thereof.

The sample cell 30 defines a sample chamber 28.14 therein. It has two quartz windows K1 and K2. Cell 30 can be made of chemically inert material, e.g. solid plastic, or stainless steel. Cell 30 can be inserted into and removed from an autoclave body 28.8, which is formed with a cylindrical opening 33 into which the cell 30 can be inserted. The cell is pushed into the autoclave opening 33 and kept in position by a screw 35, engaging a matching notch 34 (FIGS. 2A, 2B) on the cell body. The cell is open at the top to provide a fill opening 36. After filling the cell, the fill opening 36 is closed off by a thin plastic membrane 28.13 which is held in position by a screwed-in holding ring 38, similarly to a nut.

The outer dimensions of the autoclave cell 30 are about the same as those of conventional temperature jump cells, or of the cell described in the cross-referenced U.S. Pat. No. 3,935,727, by the inventors hereof, so that the optical arrangement can be used with already existing equipment without modification. The relaxation times can be calculated on-line by a computer. The cell 30 shown in FIGS. 1A to 1C is placed in an optical path, schematically indicated by the arrows P, P'. A beam of light is beamed in the direction of the arrows P, P', generated by a suitable preferably monochromatic source, to impinge on an optical sensor and evaluation apparatus S. The optical signal can be evaluated electrically, for example by including a photomultiplier, a photo-transistor, photodiode, or the like, in the reception path P', and connecting the output, through suitable amplifiers, to an oscilloscope, data processing or recording apparatus, or the like. The membrane 28.13 which transfers the pressure jump upon release of pressure in the chamber 28.12 may have a diameter of about 8.5 mm and a thickness of approximately ¼ mm, and is made of soft plastic material.

Various chambers and modifications may be made.

We claim:

1. Apparatus for investigating fast chemical reactions in liquid samples by the pressure jump relaxation method using optical detection, comprising a housing (28.8; ), a sample cell (30) forming an autoclave sample chamber (28.14) and an auxiliary pressure chamber (28.12; ) in said housing, said sample chamber holding a liquid sample, the relaxation pressure characteristics of which are to be investigated;

at least two optical windows (K1, K2; ) sealed to said sample chamber to permit placing the chamber in an optical detection beam path (P, P');

an elastic membrane (28.13; ) sealingly separating said chambers;

said pressure chamber being formed with an opening (28.11);

a rupturable membrane (28.7;) closing the pressure chamber opening (28.11);

pressure generating means (28.23;) leading to said pressure chamber (28.12;)

a pressure head (28.3) engageable with said rupturable membrane (28.7) to seal the rupturable membrane to said opening (28.11) of said pressure chamber (28.1;);

a pressure head (28.3) having a bayonet end (28.4);

and a bayonet socket (28.5) formed on part of the body (28.8;) of said sample cell to provide for quick release and quick engagement of the rupturable membrane (28.7;) sealing the opening and permitting rapid replacement of the ruptured section of said membrane.

2. Apparatus according to claim 1, wherein said rupturable membrane comprises a strip or sheet of thin membrane material;

a gap, or notch or channel (28.26) formed within the body (28.8) to receive the strip or sheet of membrane material (28.7) and to permit selectively placing a fresh zone (49) of said material over said opening (28.11) after rupture thereof by subsequent release of said bayonet pressure head (28.3), replacement of material of said membrane, and subsequent closing off of said pressure chamber (28.12) by the replaced fresh membrane material and reclosing of said bayonet pressure head (28.3).

3. Apparatus according to claim 1, wherein said sample cell body (28.2) is formed with a mounting means (8.4);

and means (28.25) temperature controlling said sample cell.

4. Apparatus according to claim 1, wherein the gap (28.26) in which said strip-like rupturable membrane (28.7) fits is a tub-like gap (28.26).

5. Apparatus according to claim 1, wherein said pressure head is hollow; a movable piston (28.1) facing said rupturable membrane at its side opposite to said opening of said pressure chamber in the pressure head to provide, when in its withdrawn position, an air pressure level in the pressure head which is very low compared to atmospheric pressure.

6. Apparatus according to claim 1, wherein said cell (30) forming the sample chamber (28.14) comprises a body of chemically inert material.

7. Apparatus according to claim 6, wherein the sample cell body (30) is of solid plastic material.

8. Apparatus according to claim 6, wherein the sample cell body (30) is metal.

9. Apparatus according to claim 1, further comprising a pressure liquid in the pressure chamber (28.12).

10. Apparatus according to claim 9, wherein the pressure liquid is water.

11. Apparatus according to claim 1, wherein the pressure generating means comprises a duct connection (28.23) to supply pressurized liquid to said pressure chamber (28.12).

12. Apparatus according to claim 10, further comprising a pressure transducer (28.9) located in the housing in pressure transducing relation to the auxiliary pressure chamber (28.12).

13. Apparatus according to claim 1, wherein said housing (28.8) is formed with a cell receiving aperture;

said cell is a separable element comprising a cell body, said cell body having opposed windows (K1, K2) extending in said optical beam path (P, P');

said cell body being formed with the sample chamber (28.14), an opening (36) formed in said sample chamber, and an elastic membrane (28.13) being sealed to said opening;

and interengaging locking means (34, 35) formed on said cell body (30) and said housing (45) to lock the cell body in position in the housing.

14. Apparatus according to claim 13, wherein the cell body is an essentially tubular element, the aperture in the housing being an essentially cylindrical bore, the tubular element fitting into said bore;

and wherein the windows (K1, K2) are located transversely to the major axis of the tubular element.

15. Apparatus according to claim 14, wherein said windows are located in essentially parallel planes, and said opening (36) is located in a plane transverse to the planes of said windows (K1, K2);

and said elastic membrane (28.13) is removably secured in said opening.

16. Apparatus according to claim 15, further comprising a screw ring (38) securing the membrane (28.13) in said opening.

* * * * *